United States Patent
Saitou

(10) Patent No.: US 10,145,795 B2
(45) Date of Patent: Dec. 4, 2018

(54) LIGHT DETECTION APPARATUS

(71) Applicant: FUJIFILM Corporation, Tokyo (JP)

(72) Inventor: Masato Saitou, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 159 days.

(21) Appl. No.: 15/436,763

(22) Filed: Feb. 18, 2017

(65) Prior Publication Data
US 2017/0248520 A1 Aug. 31, 2017

(30) Foreign Application Priority Data
Feb. 26, 2016 (JP) .................................. 2016-035057

(51) Int. Cl.
| | |
|---|---|
| H01L 27/00 | (2006.01) |
| G01N 21/64 | (2006.01) |
| G01J 1/02 | (2006.01) |
| G01J 1/04 | (2006.01) |
| G02B 7/00 | (2006.01) |
| G01J 3/02 | (2006.01) |
| G01N 27/447 | (2006.01) |
| G01J 3/44 | (2006.01) |
| G01J 3/12 | (2006.01) |

(52) U.S. Cl.
CPC ........ G01N 21/6456 (2013.01); G01J 1/0214 (2013.01); G01J 1/0238 (2013.01); G01J 1/0403 (2013.01); G01J 1/0448 (2013.01); G01J 1/0492 (2013.01); G01J 3/0235 (2013.01); G01J 3/0275 (2013.01); G01N 27/44721 (2013.01); G02B 7/006 (2013.01); G01J 3/4406 (2013.01); G01J 2003/1217 (2013.01); G01J 2003/1221 (2013.01); G01N 2021/6419 (2013.01); G01N 2021/6421 (2013.01); G01N 2021/6471 (2013.01)

(58) Field of Classification Search
CPC .... G01J 1/0214; G01J 1/0403; G01J 1/04448; G01J 1/0492; G02B 5/205; G02B 5/28
USPC ................................ 250/208.1, 226; 257/432
See application file for complete search history.

(56) References Cited

U.S. PATENT DOCUMENTS

2016/0114735 A1* 4/2016 Kwon .................... B60J 5/0468
296/43

FOREIGN PATENT DOCUMENTS

| JP | 2000056228 | 2/2000 |
| JP | 2001296395 | 10/2001 |
| JP | 2003308515 | 10/2003 |

OTHER PUBLICATIONS

"Search Report of Europe Counterpart Application", dated Jul. 7, 2017, p. 1-p. 8.

* cited by examiner

*Primary Examiner* — Kevin Pyo
(74) *Attorney, Agent, or Firm* — JCIPRNET

(57) ABSTRACT

First and second filter magazines in each of which plural filters having different transmission wavelengths from each other are arranged in a row are provided, and the first and second filter magazines are arranged next to each other in one direction. A light detection unit in which plural photomultipliers of first and second photomultipliers, each of which detects light that has passed through at least one of the filters included in the first and second filter magazines, are arranged in the arrangement direction of the filters is provided, and the light detection unit is placed in the one direction in such a manner to be parallel to the first and second filter magazines. The apparatus is configured in such a manner that the first and second filter magazines and the light detection unit are movable in the arrangement direction of the filters.

11 Claims, 17 Drawing Sheets

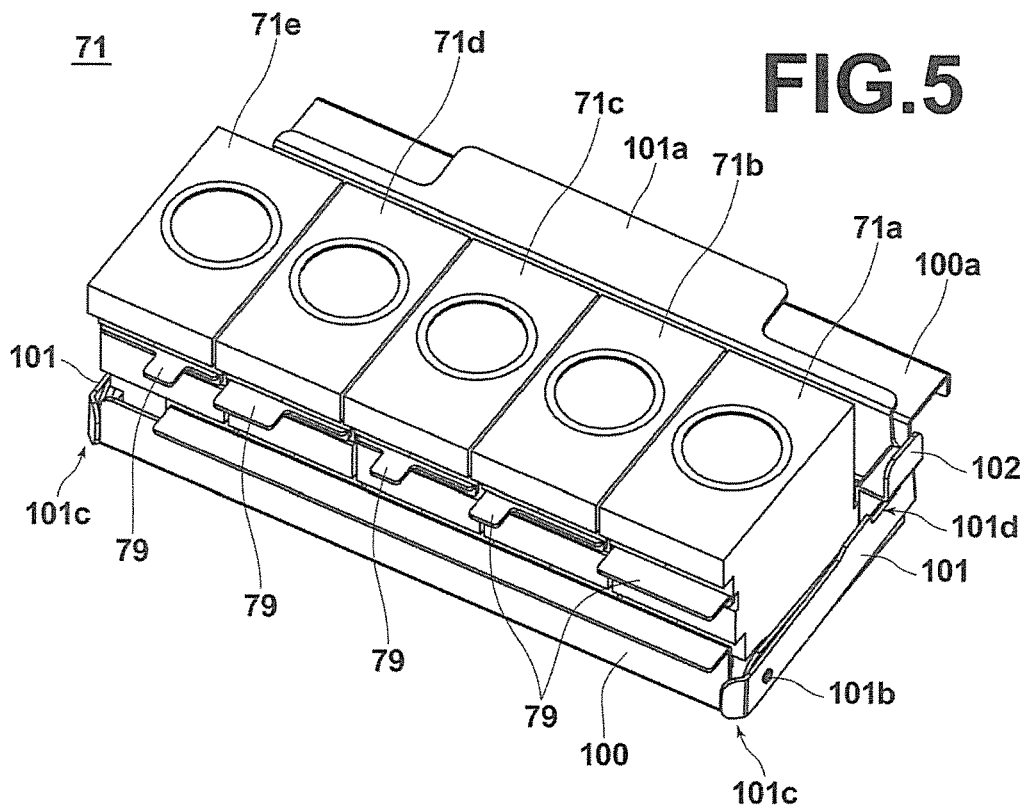
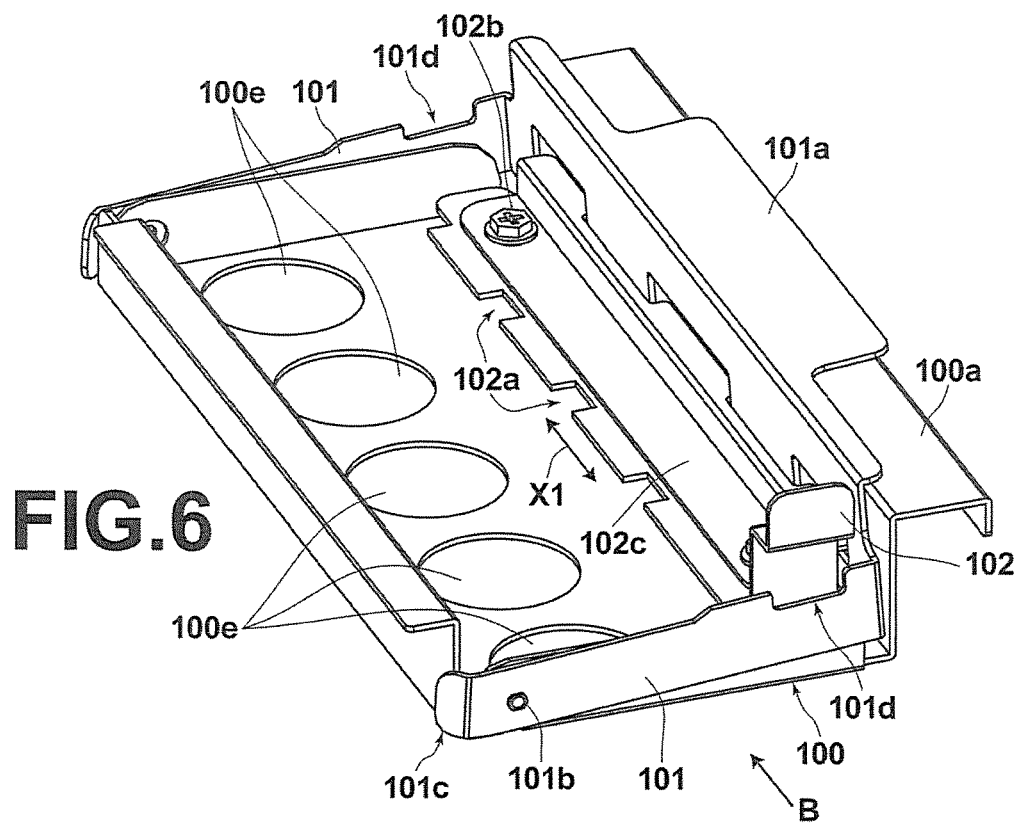

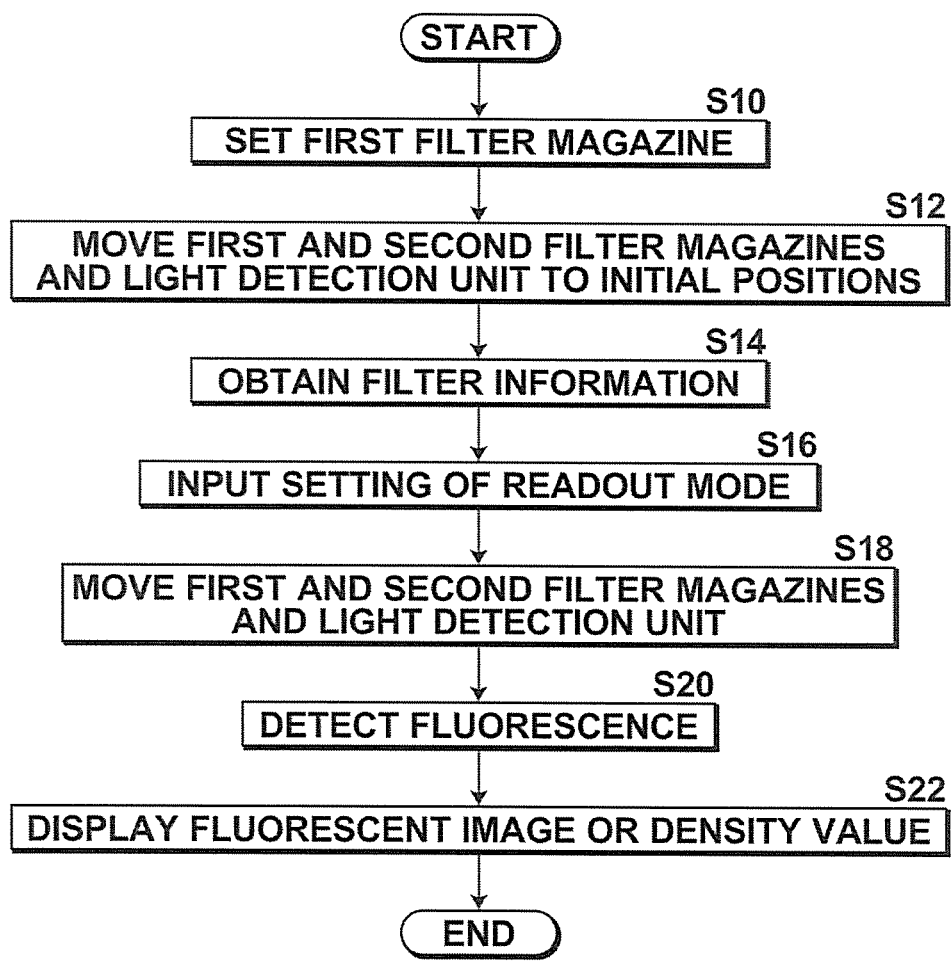

LIGHT DETECTION APPARATUS

CROSS-REFERENCE TO RELATED APPLICATIONS

The present application claims priority under 35 U.S.C. § 119 to Japanese Patent Application No. 2016-035057, filed on Feb. 26, 2016. The above application is hereby expressly incorporated by reference, in its entirety, into the present application.

BACKGROUND

The present disclosure relates to a light detection apparatus that detects light passed through a filter.

Conventionally, various image readout apparatuses for reading out fluorescent images by illuminating, with excitation light, a subject to be examined, such as a gel support body including fluorescence-labeled protein, peptide, nucleic acid and the like or a storable phosphor sheet from which a fluorescent-material-labeled substance derived from an organism has been removed after the substance was placed in close contact therewith, and by detecting fluorescence generated by illumination with the excitation light have been proposed.

Specifically, for example, Japanese Unexamined Patent Publication No. 2001-296395 (Patent Document 1) proposes an image readout apparatus that can read out fluorescent images of both a fluorescence-labeled gel support body and a storable phosphor sheet. In a case where fluorescent images of plural kinds of subjects to be examined are read out as in the image readout apparatus disclosed in Patent Document 1, the subjects to be examined need to be illuminated with excitation light having wavelengths corresponding to the kinds of the subjects to be examined, and fluorescence having different wavelengths needs to be detected, respectively.

Meanwhile, in the aforementioned image readout apparatuses, an excitation light cut filter needs to be provided on an optical path of fluorescence to prevent unwanted excitation light from entering a detector for detecting fluorescence, such as a photomultiplier. Further, in a case where the subjects to be examined are illuminated with excitation light having wavelengths corresponding to the subjects to be examined, excitation light cut filters corresponding to the wavelengths of the excitation light are needed respectively.

The image readout apparatus disclosed in Patent Document 1 proposed a structure using a dichroic mirror that separates fluorescence of different wavelength to orthogonal directions, and in which an excitation light cut filter and a detector are placed on each of a transmission optical path and a reflection optical path of fluorescence of the dichroic mirror.

SUMMARY

However, if fluorescence of different wavelengths is separated to orthogonal directions by a dichroic mirror, and an excitation light cut filter and a detector are provided on each optical path of fluorescence as in the image readout apparatus disclosed in Patent Document 1, for example, in a case where one of the optical paths of fluorescence is set in a vertical direction, a detector needs to be provided in a direction orthogonal to the vertical direction. Therefore, a space for the detector is required, and there is a problem that reduction in the size of the image readout apparatus is difficult.

Further, Japanese Unexamined Patent Publication No. 2000-56228 (Patent Document 2) and Japanese Unexamined Patent Publication No. 2003-308515 (Patent Document 3) proposed a structure in which plural rows of filter magazines, in each of which plural filters having different transmission wavelengths from each other are arranged, are placed one after another in one direction, and a filter corresponding to the wavelength of fluorescence is placed on the optical path of the fluorescence by changing the placement of the filter magazines.

However, in a case where fluorescence having different wavelengths from each other is detected, it is desirable to use a detector corresponding to the wavelength of each fluorescence. Patent Document 2 and Patent Document 3 fail to propose any structure in which such detectors for detecting fluorescence of different wavelengths are provided respectively and also the size of the whole apparatus is reducible.

In view of the foregoing circumstances, the present disclosure is directed to provide a light detection apparatus in which light having different wavelengths from each other is detectable by detectors corresponding to the wavelengths of the light respectively and also the size of the whole apparatus is reducible.

A light detection apparatus of the present disclosure includes plural filter magazines in each of which plural filters having different transmission wavelengths from each other are arranged in a row, and the plural filter magazines being arranged one after another in one direction, and a light detection unit in which plural light detectors each of which detects light that has passed through at least one of the filters included in the plural filter magazines are arranged in the arrangement direction of the filters, and the light detection unit being placed in the one direction in such a manner to be parallel to the plural filter magazines. The light detection apparatus is structured in such a manner that the plural filter magazines and the light detection unit are movable in the arrangement direction of the filters.

Further, it is desirable that the light detection apparatus of the present disclosure has a light shield tube for blocking external light at least at one position in one of the plural filter magazines that is placed toward the light detection unit.

Further, the light detection apparatus of the present disclosure may include a control unit that obtains information about the kinds of the filters included in the filter magazines, and controls, based on the information about the kinds, the positions of the filter magazines in the arrangement direction of the filters.

Further, the light detection apparatus of the present disclosure may include a filter information receiving unit that receives an input of the information about the kinds of the filters.

Further, in the light detection apparatus of the present disclosure, the filters may have filter information holding units that hold the information about the kinds of the filters.

Further, in the light detection apparatus of the present disclosure, at least one of the plural filter magazines may be structured detachably.

Further, in the light detection apparatus of the present disclosure, at least one of the plural filters included in the filter magazines may be structured in such a manner to be detachable from the filter magazines.

Further, in the light detection apparatus of the present disclosure, the plural filter magazines and the light detection unit may be placed one after another in a vertical direction.

Further, the light detection apparatus of the present disclosure may include a linear motor that moves the light detection unit.

Further, in the light detection apparatus of the present disclosure, the detachably structured filter magazine may include a filter tray on which the plural filters are placed one after another and lock levers that regulate the movement of the filter tray by being engaged with a light detection apparatus main body, and the lock levers may be rotatably provided at ends of the filter tray in the arrangement direction of the filters, and fixing portions that fix rotation shafts of the lock levers to the filter tray may be provided on inner surfaces of the ends of the filter tray.

In the light detection apparatus of the present disclosure, it is desirable that the filter magazine is mounted on the light detection apparatus main body by being inserted in a direction orthogonal to the arrangement direction of the filters, and that the lock levers are structured by members extending in the direction orthogonal to the arrangement direction of the filters, and also leading ends of the lock levers in an insertion direction to the light detection apparatus are bent inward with respect to the insertion direction.

The light detection apparatus of the present disclosure includes filter magazines in each of which plural filters having different transmission wavelengths from each other are arranged in a row, and a light detection unit in which plural light detectors are arranged in the same direction as the arrangement direction of the filters in the filter magazines, and the plural filter magazines and the light detection unit are placed parallel to each other in one direction. Further, the light detection apparatus is configured in such a manner that the plural filter magazines and the light detection unit are movable in the arrangement direction of the filters. Therefore, fluorescence having different wavelengths from each other is detectable by detectors corresponding to the wavelengths of the fluorescence respectively and also the size of the whole apparatus is reducible.

BRIEF DESCRIPTION OF THE DRAWINGS

FIG. 5 is a diagram illustrating the mechanical structure of a first filter magazine;

FIG. 6 is a diagram illustrating the structure of a filter tray and lock levers;

FIG. 19 is a flowchart for explaining the action of an image readout system using an embodiment of the light detection apparatus of the present disclosure.

DESCRIPTION OF THE PREFERRED EMBODIMENTS

Figure 1:
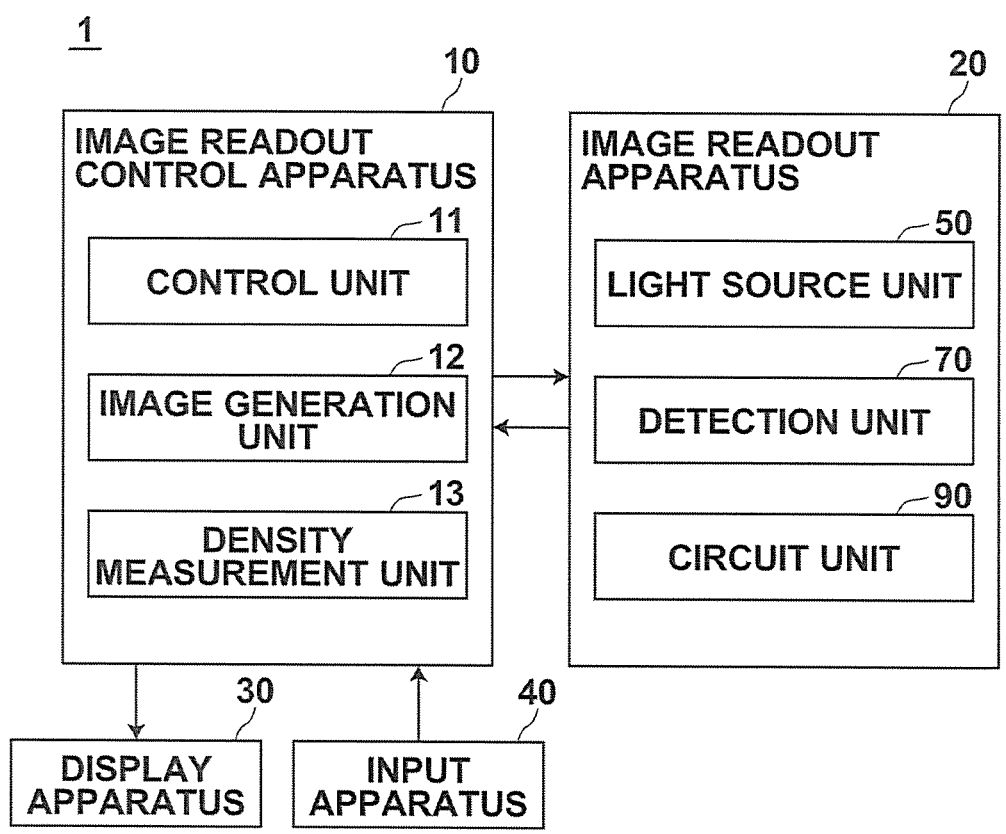
FIG. 1 is a schematic block diagram illustrating the configuration of an image readout system using an embodiment of a light detection apparatus of the present disclosure.

Next, an image readout system using an embodiment of a light detection apparatus of the present disclosure will be described in detail with reference to drawings. FIG. 1 is a schematic block diagram illustrating the configuration of an image readout system 1 of the present embodiment. The image readout system 1 of the present embodiment two-dimensionally scans a readout target with condensed laser light. After fluorescence emitted from each point of the readout target illuminated with the laser light is separated by an appropriate spectral filter, a two-dimensional image is generated by condensing the light onto a light detector, such as a photomultiplier.

The image readout system 1 of the present embodiment includes an image readout control apparatus 10, an image readout apparatus 20, a display apparatus 30 and an input apparatus 40, as illustrated in FIG. 1.

The image readout control apparatus 10 is configured by a computer including a CPU (Central Processing Unit), a memory, a hard disk and the like. These configure a control unit 11, an image generation unit 12 and a density measurement unit 13, illustrated in FIG. 1. Each of these units will be described later in detail.

The image readout apparatus 20, the display apparatus 30 and the input apparatus 40 are connected to the image readout control apparatus 10. The display apparatus 30 is configured by a display device, such as a liquid crystal display. The input apparatus 40 is configured by an input device, such as a keyboard and a mouse. A touch panel may be used to function both as the display apparatus 30 and as the input device 40.

Figure 2:
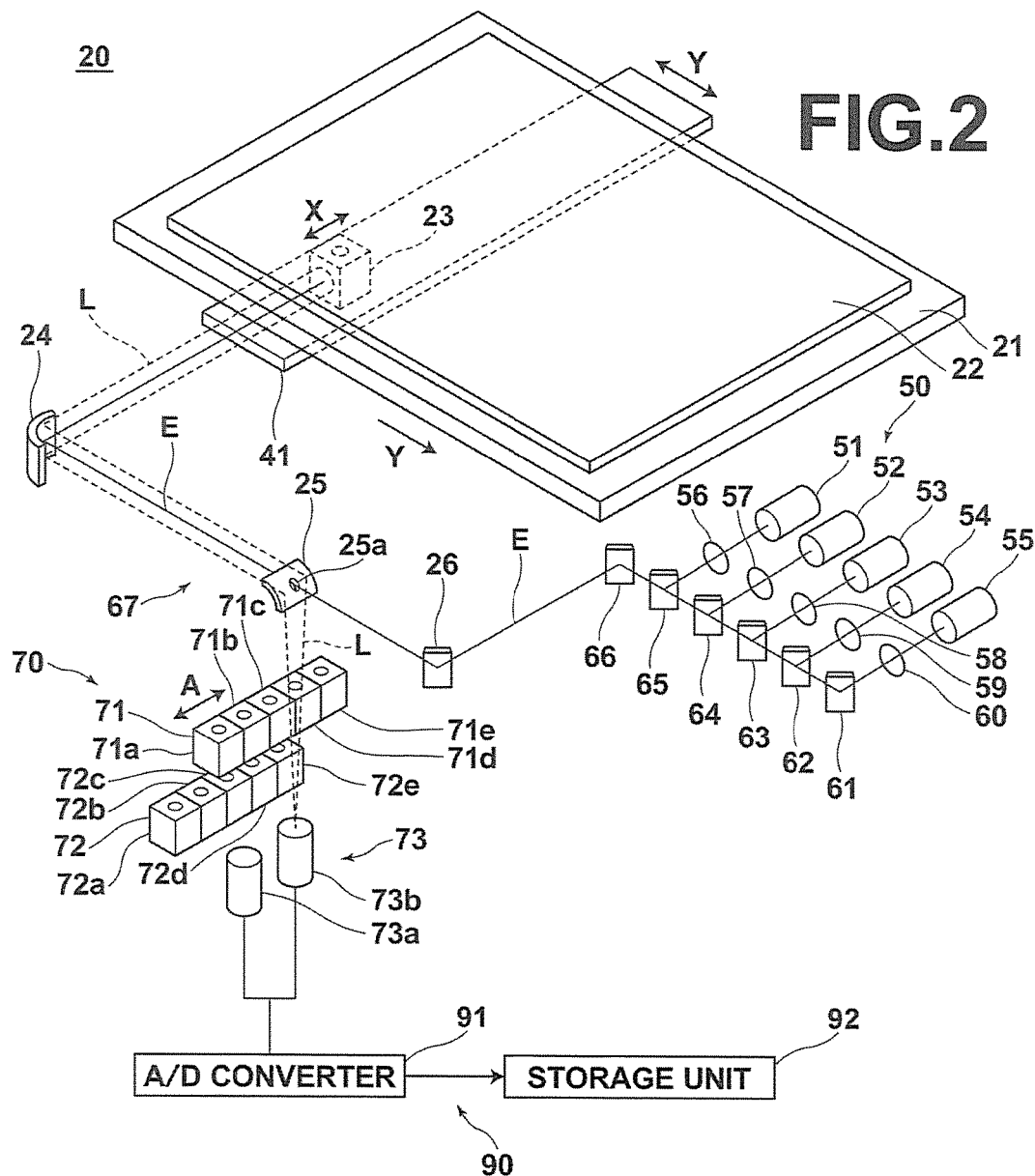
FIG. 2 is a schematic diagram illustrating the configuration of an image readout apparatus.

FIG. 2 is a schematic diagram illustrating the configuration of the image readout apparatus 20. The image readout apparatus 20 includes a subject-to-be-examined support unit 21, a light source unit 50, a detection unit 70, an optical system 67 and a circuit unit 90, as illustrated in FIG. 2. In the present embodiment, the light detection apparatus of the present disclosure is configured by the control unit 11 in the image readout control apparatus 10 and the detection unit 70 in the image readout apparatus 20.

A sample 22, which corresponds to the subject to be examined, is set on the subject-to-be-examined support unit 21, and the subject-to-be-examined support unit 21 supports the sample 22. The subject-to-be-examined support unit 21 is structured by a plate-shaped member, and formed of material transparent to the wavelengths of excitation light E output from the light source unit 50 and fluorescence L emitted from the sample 22. Specifically, for example, the subject-to-be-examined support unit 21 is made of transparent resin, glass or the like.

The sample 22 is, for example, a gel support body including fluorescence-labeled protein, peptide, nucleic acid and the like, a storable phosphor sheet from which a fluorescent-material-labeled substance derived from an organism has been removed after the substance was placed in close contact therewith and the like. The image readout apparatus 20 of the present embodiment is configured in such a manner that a gel support body using each of IRDye680®, IRDye800®, Cy2, Cy3 and Cy5 and a storable phosphor sheet are readable, as the sample 22. As will be described later in detail, other fluorescent images are also readable by changing filters constituting first and second filter magazines 71, 72.

The light source unit 50 includes a first excitation light source 51 that outputs excitation light E with the center wavelength of 488 nm, a second excitation light source 52 that outputs excitation light E with the center wavelength of 532 nm, a third excitation light source 53 that outputs excitation light E with the center wavelength of 635 nm, a fourth excitation light source 54 that outputs excitation light E with the center wavelength of 685 nm, and a fifth excitation light source 55 that outputs excitation light E with the center wavelength of 785 nm. In the present embodiment, the first excitation light source 51 through the fifth excitation light source 55 are structured by semiconductor laser light sources and second harmonic generation devices (Second Harmonic Generation), or semiconductor laser light sources. Here, the center wavelengths of excitation light output from the first through fifth excitation light sources 51 through 55 are not necessarily the aforementioned values, and may be in the ranges of ±15 nm from the values of the center wavelengths.

Further, the light source unit 50 includes collimator lenses 56, 57, 58, 59 and 60 for collimating excitation light E output from the first through fifth excitation light sources 51 through 55, and mirrors 61, 66 and first through fourth dichroic mirrors 62, 63, 64 and 65 for guiding excitation light E to the optical system 67.

The first dichroic mirror 62 transmits excitation light E of 785 nm or longer and reflects light having the wavelength of 685 nm. The second dichroic mirror 63 transmits excitation light of 685 nm or longer and reflects light having the wavelength of 635 nm. The third dichroic mirror 64 transmits excitation light of 635 nm or longer and reflects light having the wavelength of 532 nm. The fourth dichroic mirror 65 transmits excitation light of 532 nm or longer and reflects light having the wavelength of 488 nm.

Excitation light E output from the first excitation light source 51 is collimated by the collimator lens 56. After then, the direction of excitation light E is changed by 90 degrees by being reflected by the fourth dichroic mirror 65, and excitation light E enters the mirror 66.

Excitation light E output from the second excitation light source 52 is collimated by the collimator lens 57. After then, the direction of excitation light E is changed by 90 degrees by being reflected by the third dichroic mirror 64, and excitation light E passes through the fourth dichroic mirror 65 and enters the mirror 66.

Excitation light E output from the third excitation light source 53 is collimated by the collimator lens 58. After then, the direction of excitation light E is changed by 90 degrees by being reflected by the second dichroic mirror 63, and excitation light E passes through the third dichroic mirror 64 and the fourth dichroic mirror 65 and enters the mirror 66.

Excitation light E output from the fourth excitation light source 54 is collimated by the collimator lens 59. After then, the direction of excitation light E is changed by 90 degrees by being reflected by the first dichroic mirror 62, and excitation light E passes through the second through fourth dichroic mirrors 63 through 65 and enters the mirror 66.

Excitation light E output from the fifth excitation light source 55 is collimated by the collimator lens 60. After then, the direction of excitation light E is changed by 90 degrees by being reflected by the mirror 61, and excitation light E passes through the first through fourth dichroic mirrors 62 through 65 and enters the mirror 66.

Each of first through fifth excitation light sources 51 through 55 is used by being switched between readout of a fluorescent image of a fluorescence-labeled gel support body and readout of a fluorescent image of a storable phosphor sheet. Specifically, in a case where a fluorescent image of a gel support body using Cy2 is read out, the first excitation light source 51 is used, because the excitation wavelength of Cy2 is 489 nm. In a case where a fluorescent image of a gel support body using Cy3 is read out, the second excitation light source 52 is used, because the excitation wavelength of Cy3 is 550 nm. In a case where a fluorescent image of a gel support body using Cy5 is read out, the third excitation light source 53 is used, because the excitation wavelength of Cy5 is 643 nm. In a case where a fluorescent image of a gel support body using IRDye680 is read out, the fourth excitation light source 54 is used, because the excitation wavelength of IRDye680 is 672 nm. In a case where a fluorescent image of a gel support body using IRDye800 is read out, the fifth excitation light source 55 is used, because the excitation wavelength of IRDye800 is 774 nm. Further, in a case where a fluorescent image of a storable phosphor sheet is read out, the third excitation light source 53 is used, because the excitation wavelength is 640 nm.

Excitation light E that has entered the mirror 66 is reflected by the mirror 66, and enters a mirror 26 in the optical system 67.

The optical system 67 includes the aforementioned mirror 26, a mirror 25 with a hole and a concave mirror 24. The mirror 25 with a hole splits excitation light E and fluorescence L emitted from the sample 22, and is structured by a concave mirror having a hole 25a at its central part.

Excitation light E that has been reflected by the mirror 66 in the light source unit 50 and entered the mirror 26 in the optical system 67 is reflected by the mirror 26 in the optical system 67. The reflected light passes through the hole 25a of the mirror 25 with the hole, and enters the concave mirror 24. The light is reflected by the concave mirror 24, and enters an optical head 23.

The optical head 23 includes a concave mirror and an aspheric lens, which are not illustrated. Excitation light E that has entered the optical head 23 is reflected by the concave mirror toward the subject-to-be-examined support unit 21 and the sample 22, and condensed by the aspheric lens onto the sample 22 set on the subject-to-be-examined support unit 21.

The optical head 23 is attached to the optical head support substrate 41 in such a manner to be movable in the longitudinal direction (X direction) of the optical head support substrate 41. Further, the optical head support substrate 41 is provided in such a manner to be movable in a direction (Y direction) orthogonal to the longitudinal direction by a movement mechanism, which is not illustrated.

The optical head support substrate 41 moves in Y direction, and also the optical head 23 moves in X direction at each position of the optical head support substrate 41 in Y direction. Accordingly, the entire area of the sample 22 is scanned with excitation light E.

Fluorescence L emitted from an excitation light illumination position on the sample 22 passes through the subject-to-be-examined support unit 21, and enters the optical head 23.

Fluorescence L that has entered the optical head 23 is condensed by the aspheric lens in the optical head 23, and enters the concave mirror in the optical head 23. Fluorescence L is reflected by the concave mirror toward the same side as the optical path of excitation light E, and collimated, and enters the concave mirror 24 in the optical system 67.

Fluorescence L that has entered the concave mirror 24 is reflected by the concave mirror 24, and enters the mirror 25 with a hole. Fluorescence L that has entered the mirror 25 with a hole is reflected by the mirror 25 with a hole toward the detection unit 70.

The detection unit 70 includes a first filter magazine 71, a second filter magazine 72 and a light detection unit 73. Fluorescence L that has been reflected by the mirror 25 with a hole enters the first filter magazine 71 and/or the second filter magazine 72, and light having unwanted wavelengths is cut. Then, the light enters the light detection unit 73, and is photoelectrically detected.

The first filter magazine 71 includes a first filter 71a, second filter 71b, a third filter 71c, a fourth filter 71d and a fifth filter 71e. The first through fifth filters 71a through 71e are placed in a row, as illustrated in FIG. 2.

The second filter magazine 72 includes a light shield tube 72a, a sixth filter 72b, a seventh filter 72c, an eighth filter 72d and a ninth filter 72e. The light shield tube 72a and the sixth through ninth filters 72b through 72e are placed also in a row in the same direction as the arrangement direction of the first through fifth filters 71a through 71e in the first filter magazines 71.

The first filter magazine 71 and the second filter magazine 72 are arranged next to each other in one direction (the incident direction of fluorescence L). The first filter magazine 71 and the second filter magazine 72 are structured in such a manner that fluorescence L that has passed through one of the filters in the first filter magazine 71 is able to pass through the light shield tube 72 or one of the filters in the second filter magazine 72. Further, the first and second filter magazines 71, 72 are structured in such a manner to be movable in the direction of arrow A in FIG. 2 independently from each other.

The light detection unit 73 includes two light detectors, i.e., a first photomultiplier 73a and a second photomultiplier 73b. The first photomultiplier 73a and the second photomultiplier 73b have different sensitive wavelength bands from each other. The first photomultiplier 73a has sensitivity in a relatively short wavelength band, and the second photomultiplier 73b has sensitivity in a relatively long wavelength band. Specifically, the first photomultiplier 73a of the present embodiment has high sensitivity to blue fluorescence L, and the second photomultiplier 73b of the present embodiment has high sensitivity to red fluorescence L. In the present embodiment, the light detection unit 73 is structured by the two photomultipliers. Alternatively, the light detection unit 73 may be structured by three or more photomultipliers.

The first photomultiplier 73a and the second photomultiplier 73b are arranged in the same direction as the arrangement direction of the filters in the first and second filter magazines 71, 72. Further, the light detection unit 73 is placed in the same direction as the arrangement direction of the first and second filter magazines 71, 72 (the aforementioned one direction) in such a manner to be parallel to the first and second filter magazines 71, 72.

Specifically, the first filter magazine 71, the second filter magazine 72 and the light detection unit 73 are placed parallel to each other in one direction (the incident direction of fluorescence L). The apparatus is configured in such a manner that fluorescence L that has passed through at least one of the filters constituting the first filter magazine 71 and the second filter magazine 72 enters the first photomultiplier 73a or the second photomultiplier 73b, which constitutes the light detection unit 73. Further, the light detection unit 73 is structured in such a manner to be movable in the direction of arrow A in FIG. 2 independently from the first and second filter magazines 71, 72.

The first through fifth filters 71a through 71e and the sixth through ninth filters 72b through 72e include optical filters that cut excitation light E and transmit fluorescence L, and are placed in front of the first photomultiplier 73a or the second photomultiplier 73b selectively based on a readout mode. Accordingly, only fluorescence L to be detected is photoelectrically detected by the first or second photomultiplier 73a, 73b.

Here, the light shield tube 72a in the second filter magazine 72, unlike the sixth through ninth filters 72b through 72e, does not include an optical filter that cuts excitation light E and transmits fluorescence L. The light shield tube 72a includes a hollow tubular member that blocks external light, instead of an optical filter, and is structured in such a manner to merely transmit fluorescence L that has passed through one of the filters in the first filter magazine 71.

In the present embodiment, the first filter magazine 71, the second filter magazine 72 and the light detection unit 73 are placed in one direction (the incident direction of fluorescence L) in such a manner to be parallel to each other, as described above. Therefore, for example, in a case where fluorescence L is detected by using only one of the filters in the first filter magazine 71, a space is formed between the filter and the light detection unit 73. Hence, there is a risk that external light is diffracted at this space and enters the light detection unit 73, and a noise is generated.

Therefore, in the present embodiment, the light shield tube 72a is placed in the second filter magazine 72. In a case where fluorescence L is detected by using only one of the filters in the first filter magazine 71, the light shield tube 72a is placed at an exit of the filter through which fluorescence L is output. Such structure can prevent the aforementioned diffracted external light from entering the light detection unit 73.

Meanwhile, in the present embodiment, the sixth through ninth filters 72b through 72e are tubular members made of material that blocks external light, and in which optical filters are provided. As the light shield tube 72, the same member as the members of the sixth through ninth filters 72b through 72e from which the optical filters are removed is used.

Further, the aforementioned readout mode is set in advance based on the kind of a readout target or the like. Each readout mode and the combination of a filter or filters, a light shield tube 72a and a photomultiplier used in each readout mode will be described later in detail.

The circuit unit 90 includes an A/D converter 91 and a storage unit 92. The A/D converter 91 converts an analog image signal output from the first or second photomultiplier 73a, 73b into a digital image signal. Further, the storage unit 92 is configured by a semiconductor memory or the like, and stores the digital image signal output from the A/D converter 91. The digital image signal stored in the storage unit 92 is output to the image readout control apparatus 10.

Figure 3:
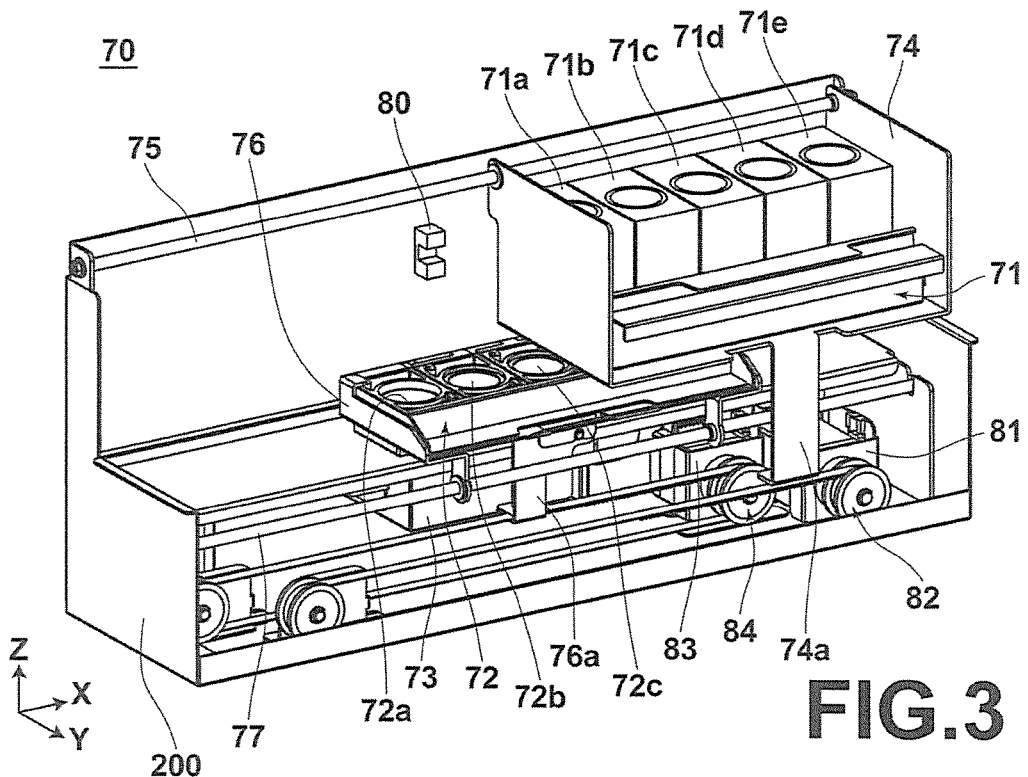
FIG. 3 is a diagram illustrating the mechanical structure of a detection unit.

Here, the mechanical structure of the detection unit 70 will be described more in detail with reference to FIG. 3 through FIG. 9. FIG. 3 is a schematic perspective view illustrating the configuration of the whole detection unit 70. In FIG. 3, Z direction is the vertical direction, and X direction and Y direction are orthogonal to each other in the horizontal direction. Further, X direction illustrated in FIG. 3 is the same direction as the direction of arrow A illustrated in FIG. 2. X direction and Y direction illustrated in FIG. 3 may be the same directions as X direction and Y direction illustrated in FIG. 2, or different directions. Further, in the following descriptions, the upper side of the vertical direction (Z direction) is regarded as "upper", and the lower side of the vertical direction (Z direction) is regarded as "lower". The positive direction (the direction of the arrow) of X direction is regarded as "right", and the negative direction of X direction is regarded as "left". The positive direction (the direction of the arrow) of Y direction is regarded as "front", and the negative direction of Y direction is regarded as "rear".

As illustrated in FIG. 3, the detection unit 70 includes a casing 200 in which the first filter magazine 71, the second filter magazine 72 and the light detection unit 73 are set. The first filter magazine 71, the second filter magazine 72 and the light detection unit 73 are set parallel to each other in the vertical direction in the casing 200.

A first shaft 75 extending in X direction is provided in an upper stage of the casing 200, and a first fixing rack 74 is provided for this first shaft 75. The first fixing rack 74 is set slidably along the first shaft 75, and the first filter magazine 71 is set detachably in this fixing rack 74.

The first fixing rack 74 is connected to a first conveyance belt mechanism 82 through a first connection member 74a. The first conveyance belt mechanism 82 is structured by a conveyance belt extending in X direction and two pulleys provided at both ends of the conveyance belt, and a drive motor 81 is connected to the pulley on the drive side. Further, the first conveyance belt mechanism 82 is driven by this drive motor 81. Accordingly, the first fixing rack 74 moves in X direction. The drive motor 81 rotates based on a control signal output from the control unit 11 in the image readout control apparatus 10.

Further, a second shaft 77 extending in X direction is provided in a lower stage of the casing 200, and a second fixing rack 76 is provided for this second shaft 77. The second fixing rack 76 is set slidably along the second shaft 77, and the second filter magazine 72 is fixedly set in this second fixing rack 76. Here, the light shield tube 72a and the sixth through ninth filters 72n through 72e in the tray of the second filter magazine 72 are structured in such a manner to be individually detachable.

The second fixing rack 76 is connected to a second conveyance belt mechanism 84 through a second connection member 76a. The second conveyance belt mechanism 84 is structured by a conveyance belt extending in X direction and two pulleys provided at both ends of the conveyance belt, and a drive motor 83 is connected to the pulley on the drive side. Further, the second conveyance belt mechanism 84 is driven by this drive motor 83. Accordingly, the second fixing rack 76 moves in X direction. The drive motor 83 rotates based on a control signal output from the control unit 11 in the image readout control apparatus 10.

Figure 4:
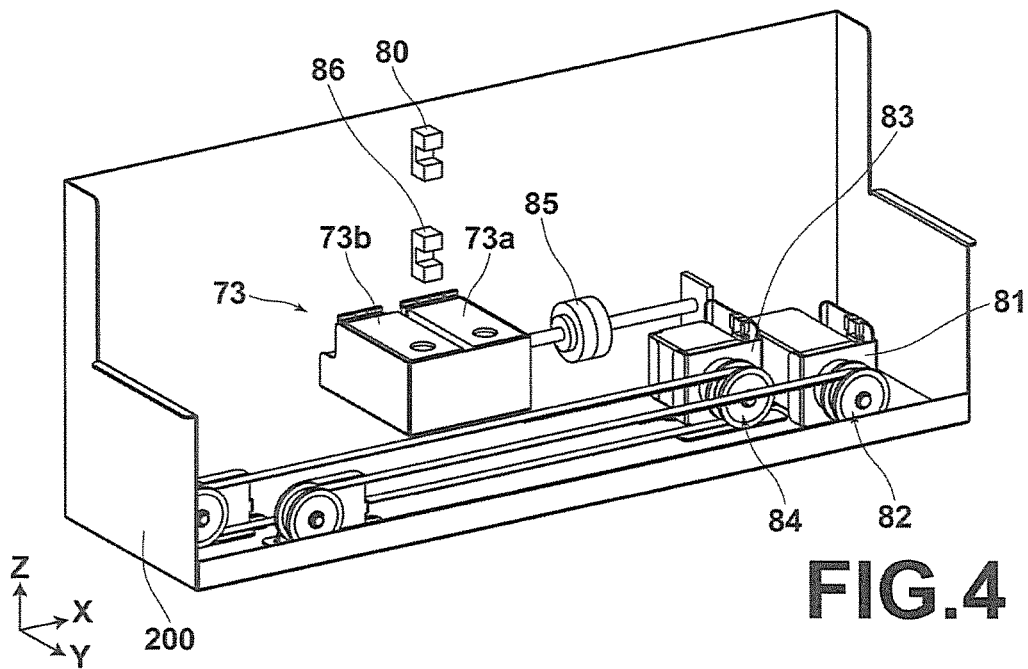
FIG. 4 is a diagram illustrating the mechanical structure of the detection unit.

Next, FIG. 4 is a perspective view illustrating a state in which an upper part including the first filter magazine 71 and the second filter magazine 72 illustrated in FIG. 3 has been removed. As illustrated in FIG. 4, the light detection unit 73 including the first photomultiplier 73a and the second photomultiplier 73b is placed under the second filter magazine 72. A linear motor 85 is connected to the light detection unit 73, and the light detection unit 73 moves in X direction by this linear motor 85. The linear motor 85 is driven based on a control signal output from the control unit 11 in the image readout control apparatus 10. The width in Y direction is reducible by using the linear motor 85 in this manner, compared with a case of using a conveyance belt mechanism. Accordingly, the size of the detection unit 70 is reducible.

FIG. 5 is a diagram illustrating the structure of the first filter magazine 71 more in detail. The first filter magazine 71 includes a filter tray 100 on which the first through fifth filters 71a through 71e are placed one after another. The filter tray 100 is formed in the shape of a dish having a side wall portion. A handle portion 100a is formed at an edge of the filter tray 100 extending in the longitudinal direction (the arrangement direction of the filters) so that a user can easily grasp the first filter magazine 71. The first filter magazine 71 is inserted to the first fixing rack 74 from a side opposite to a side on which the handle portion 100a is formed.

Further, lock levers 101 are provided at both ends of the filter tray 100 in the arrangement direction of the first through fifth filters 71a through 71e. The lock lever 101 is structured by a member extending in a direction orthogonal to the arrangement direction of the first through fifth filters 71a through 71e.

FIG. 6 is a diagram illustrating a state in which the first through fifth filters 71a through 71e have been removed from the first filter magazine 71 illustrated in FIG. 5. As illustrated in FIG. 6, holes 100e for transmitting fluorescence L that has passed through the first through fifth filters 71a through 71e are formed in a bottom of the filter tray 100. Further, as illustrated in FIG. 5 and FIG. 6, the lock levers 101 are provided on the outer surfaces of both ends of the filter tray 100. Further, the two lock levers 101 are structured in an integrated manner by being connected to each other by a coupling member 101a. As illustrated in FIG. 5 and FIG. 6, cutout portions 101d are formed on the lock levers 101.

Further, as illustrated in FIG. 6, a filter holding lever 102 is provided in the filter tray 100. The filter holding lever 102 is placed between a plate member 102c and a bottom of the filter tray 100, and attached the bottom of the filter tray 100 by a nut portion 102b. The filter holding lever 102 is provided slidably in the direction of arrow X1 between the plate member 102c and the bottom of the filter tray 100. Further, plural recesses 102a are formed on the filter holding lever 102 along the longitudinal direction of the filter holding lever 102. The apparatus is structured in such a manner that the first through fifth filters 71a through 71e are held by the recesses 102a by sliding the filter holding lever 102 in the direction of arrow X1.

Figure 7:
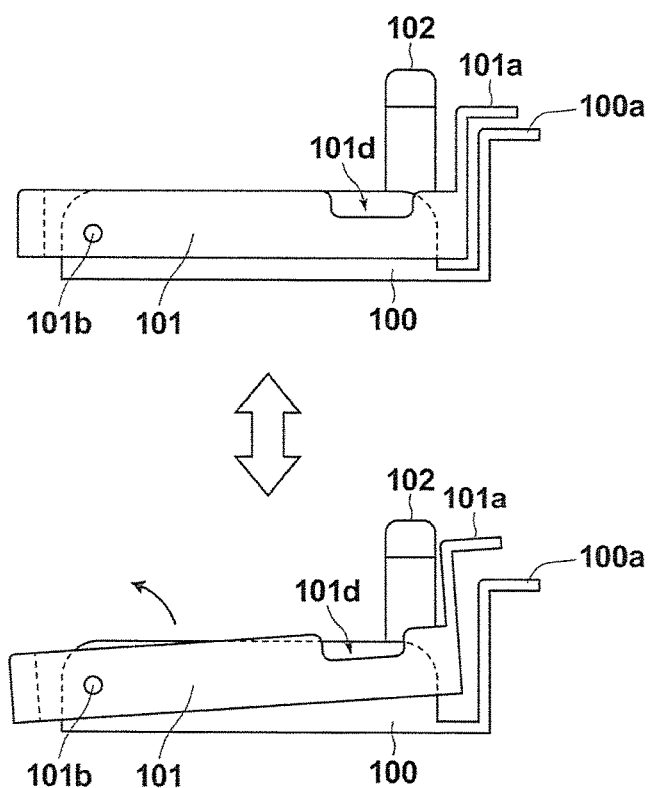
FIG. 7 is a diagram for explaining rotation of a lock lever.

Further, an end of the lock lever 101 (an end opposite to a side connected to the coupling member 101a) is provided rotatably with respect to the filter tray 100. Accordingly, the lock lever 101 rotates on a rotation shaft 101b, as a center. As the lock lever 101 rotates, the coupling member 101a also rotate together with the lock lever 101. FIG. 7 is a diagram viewing FIG. 6 from the direction of arrow B, and illustrates rotation of the lock lever 101.

The lock levers 101 and the coupling member 101a are energized upward by an elastic member, such as a spring, which is not illustrated. In a case where a user attaches the filter tray 100 on which the first through fifth filters 71a through 71e are set to the detection unit 70 main body (the light detection apparatus main body) illustrated in FIG. 3, the filter tray 100 is inserted to the first fixing rack 74 in a state in which the coupling member 101a is pressed down by the user. After the filter tray 100 is inserted to the first fixing rack 74, the lock lever 101 moves upward by being energized by the aforementioned elastic member, and the cutout portion 101d formed on the lock lever 101 engages with a lock pin 103 (please refer to FIG. 8) provided on the detection unit 70 main body. The movement of the filter tray 100 in the insertion direction is regulated by this engagement of the cutout portion 101d with the lock pin 103. Meanwhile, in a case where the filter tray 100 is detached from the detection unit 70 main body, the coupling member 101a is pressed down by the user.

Figure 8:
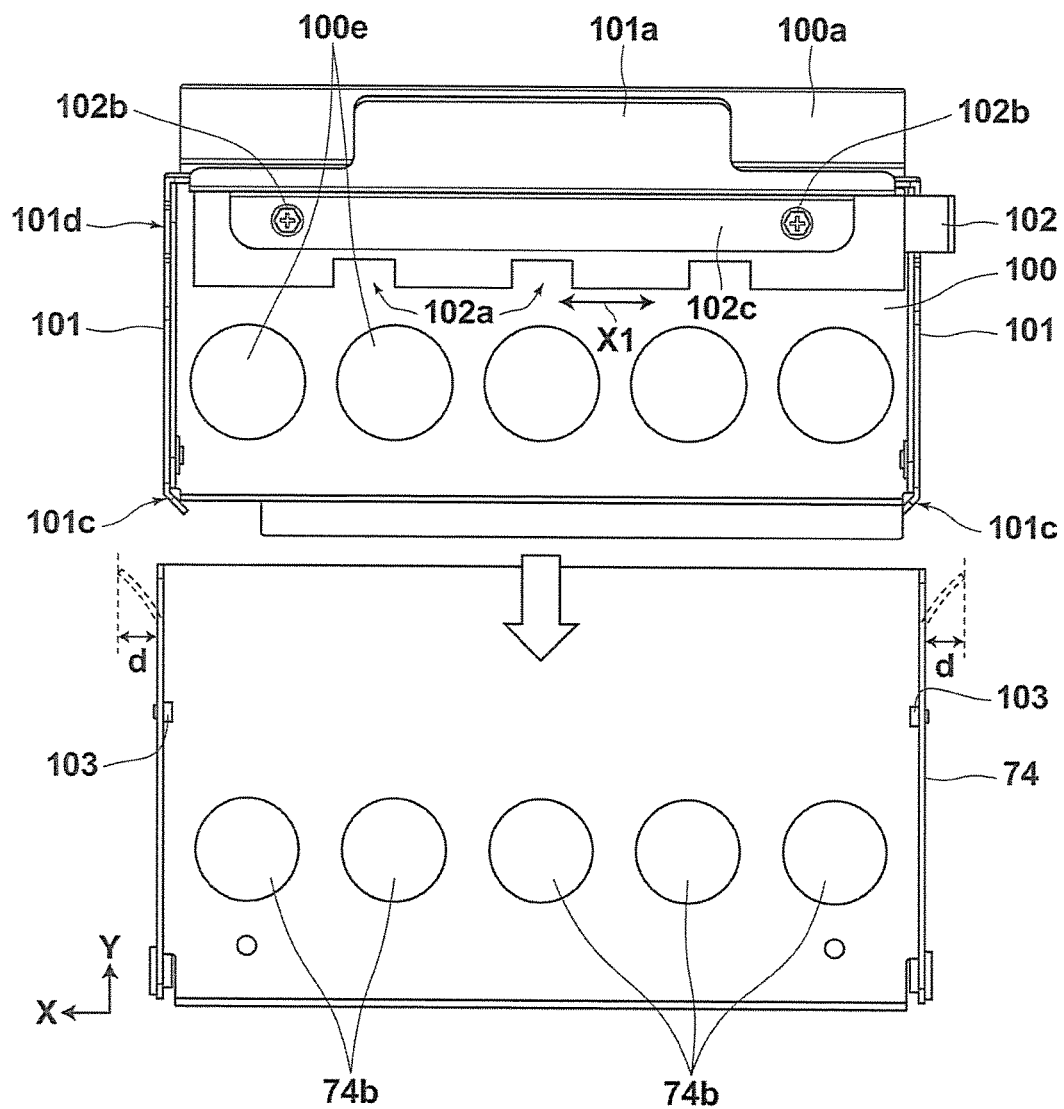
FIG. 8 is a diagram for explaining the action of a guide portion provided on the lock lever.

Further, a guide portion 101c is formed at a leading end portion of the lock lever 101 in an insertion direction to the detection unit 70 main body, as illustrated in FIG. 5 and FIG. 6. The guide portion 101c is forming by bending the leading end portion of the lock lever 101 inward with respect to the insertion direction of the filter tray 100. FIG. 8 is a diagram illustrating a manner of inserting the filter tray 100 to the first fixing rack 74, and which is viewed from the upper side. As illustrated in FIG. 8, since the guide portion 101c is formed, even in a case where the leading end of the lock lever 101 in the insertion direction collides the side wall portion of the first fixing rack 74, the rock lever 101 is smoothly guidable toward the inside of the side wall portion of the filter tray 100 by the inclination of the guide portion 101c. Meanwhile, as illustrated in FIG. 8, holes 74b for transmitting fluorescence L that has passed through the first through fifth filters 71a through 71e are formed in the bottom of the first fixing rack 74. Further, the lock pin 103, which is to be engaged with the aforementioned cutout portion 101d of the lock lever 101, is provided on the inner surface of a side wall of the first fixing rack 74.

Further, as a method for preventing collision between the leading end of the lock lever 101 in the insertion direction and the side wall portion of the first fixing rack 74, an insertion opening of the side wall portion of the first fixing rack 74 may be widened outward, as indicated by a dotted line in FIG. 8, in other words, a guide portion may be formed on the first fixing rack 74 side. However, it is possible to save the space by distance d×2, illustrated in FIG. 8, by forming the guide portion 101c on the filter tray 100 side as in the present embodiment.

Figure 9:
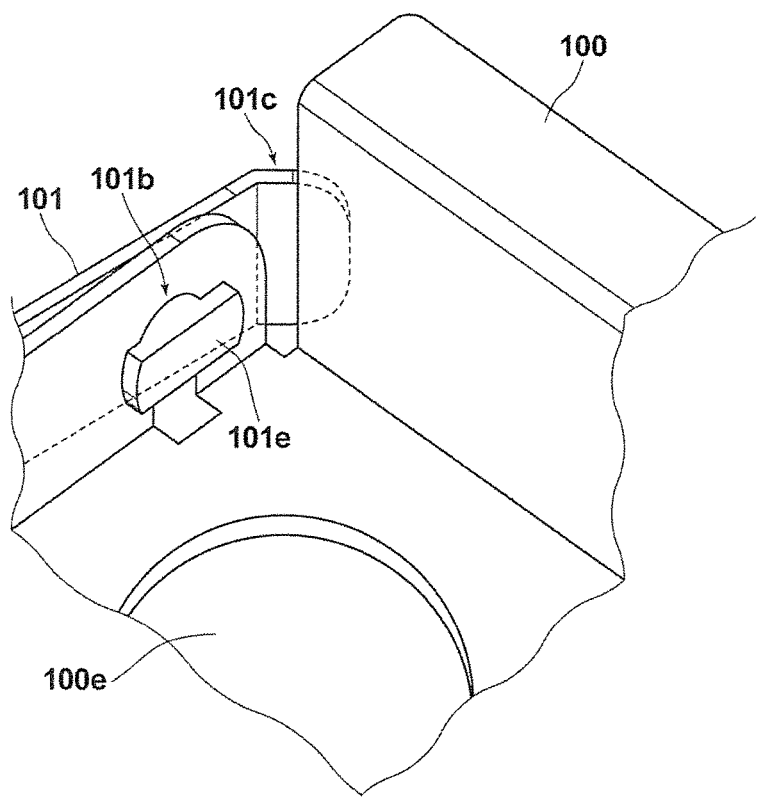
FIG. 9 is a diagram illustrating the structure of a fixing portion of the lock lever.

Further, in a case where the rotation shaft of the lock lever 101 is provided in the filter tray 100, it is desirable that a fixing portion 101e for fixing the rotation shaft 102b to the filter tray 100 is provided on the inner surface of the end of the filter tray 100, as illustrated in FIG. 9. This structure can save the space with respect to the lateral direction (a direction orthogonal to the insertion direction) of the filter tray 100, compared with a case of providing the fixing portion of the rotation shaft 102b on the outer surface of the filter tray 100.

In the present embodiment, only the first filter magazine 71 is structured detachably as described above. A similar structure may be adopted also for the second filter magazine 72, and the second filter magazine 72 may be structured detachably.

So far, the mechanical structure of the detection unit 70 has been described.

Back to FIG. 1, the image readout control apparatus 10 includes the control unit 11, the image generation unit 12 and the density measurement unit 13, as described above.

The control unit 11 controls the whole image readout system 1. Particularly, the control unit 11 controls the movement of the first filter magazine 71, the second filter magazine 72 and the light detection unit 73.

Here, the movement control of the first filter magazine 71, the second filter magazine 72 and the light detection unit 73 in the present embodiment will be described in detail. In the present embodiment, the combination of a filter or filters and a photomultiplier used is determined based on the readout mode, as described above, and the first filter magazine 71, the second filter magazine 72 and the light detection unit 73 are moved based on the combination. As a prerequisite for the movement control, the kinds of the first through fifth filters 71a through 71e in the first filter magazine 71, the kinds of the light shield tube 72a and the sixth through ninth filters 72b through 72e in the second filter magazine 72 and the kinds of the first and second photomultipliers 73a, 73b need to be known in advance.

Specifically, the first through fifth filters 71a through 71e in the first filter magazine 71 and the light shield tube 72a and the sixth through ninth filters 72b through 72e in the second filter magazine 72 are detachable, and changed by a user, if necessary.

Therefore, information about the kinds of the first through fifth filters 71a through 71e, the light shield tube 72a and the sixth through ninth filters 72b through 72e is needed to select one of the filters in the first filter magazine 71a or the second filter magazine 72 based on the readout mode, and to place the filter in front of a selected photomultiplier.

Such information may be set by an input by a user using the input apparatus 40. Alternatively, filter information holding units for holding information about the kinds of the first through fifth filters 71a through 71e, the light shield tube 72a and the sixth through ninth filters 72b through 72e may be provided for the first through fifth filters 71a through 71e, the light shield tube 72a and the sixth through ninth filters 72b through 72e. Further, the information about the kinds of the filters may be read out from the filter information holding units. Accordingly, the control unit 11 may obtain the information about the kinds of the filters and information about the positions of the filters. In the present embodiment, the input apparatus 40 corresponds to a filter information receiving unit.

In the present embodiment, a metal piece pattern 79, as illustrated in FIG. 5, is provided as the filter information holding unit. The metal piece pattern 79 is provided for each filter, and the shape of the metal piece pattern 79 is different depending on the kind of the filter. Specifically, the metal piece pattern 79 in the present embodiment represents information about the kind of a filter by the length of the metal piece pattern 79 and the position of the metal piece pattern 79 provided with respect to the filter. The length of the metal piece pattern 79 may be four kinds. Then, it is possible to represent information about 16 kinds of filters by the combination of the length and the placement of the metal piece pattern 79 with respect to the filter.

Information about the metal piece pattern 79 illustrated in FIG. 5 is read out when the metal piece pattern 79 passes a first optical sensor 80 provided on the inner wall surface of the casing 200 illustrated in FIG. 3. The information is output to the control unit 11 in the image readout control apparatus 10. The metal piece patterns 79 are provided not only for the first through fifth filters 71a through 71e in the first filter magazine 71 but also for the light shield tube 72a and the sixth through ninth filters 72b through 72e in the second filter magazine 72. The information about the metal piece patterns 79 for the light shield tube 72a and the sixth through ninth filters 72b through 72e in the second filter magazine 72 is read out by a second optical sensor 86 illustrated in FIG. 4.

In the present embodiment, the metal piece pattern 79 formed of metal is provided. However, the material of this pattern is not limited to metal, and any material may be used as long as the material has properties that block light. For example, a pattern may be forming of black resin.

Further, the filter information holding unit is not limited to the aforementioned metal piece pattern 79. For example, a bar code or an IC (Integrated Circuit) chip in which the kind of a filter is stored may be provided for each of the filters 71a through 71e and 72b through 72b and the light shield tube 72a, and the information may be read out.

Here, the light detection unit 73 is provided fixedly. Basically, the kinds of the first and second photomultipliers 73a, 73b constituting the light detection unit 73 are fixed. Therefore, information about the kinds of the first and second photomultipliers 73a, 73b is set in advance in the control unit 11.

Further, when a readout mode is set by an input by the user using the input apparatus 40, information about the readout mode is obtained by the control unit 11. The control unit 11 determines the combination of a filter or filters and a photomultiplier based on the readout mode, and controls the positions of the first and second filter magazines 71, 72 and the light detection unit 73 so that fluorescence L is detected by using the combination.

The image readout system of the present embodiment is configured in such a manner that a first fluorescent image readout mode for reading out a fluorescent image by detecting fluorescence L emitted from a storable phosphor sheet, a second fluorescent image readout mode for reading out a fluorescent image by detecting fluorescence L emitted from Cy2, which is a fluorescence label, a third fluorescent image readout mode for reading out a fluorescent image by detecting fluorescence L emitted from Cy3, which is a fluorescence label, and a fourth fluorescent image readout mode for reading out a fluorescent image by detecting fluorescence L emitted from Cy5, which is a fluorescence label, are settable.

Further, the image readout system of the present embodiment is configured in such a manner that a fifth fluorescent image readout mode for reading out a fluorescent image by detecting fluorescence L emitted from IRDye680, which is a fluorescence label, a sixth fluorescent image readout mode for reading out a fluorescent image by detecting fluorescence L emitted from IRDye800, which is a fluorescence label, a first density measurement mode for measuring a density value by detecting fluorescence L that has been emitted from a fluorescent plate set on a sample 22 and passed through a filter for detecting fluorescence of Cy3, which will be described later, and a second density measurement mode for measuring a density value by detecting fluorescence L that has been emitted from a fluorescent plate set on a sample 22 and passed through a filter for detecting fluorescence of Cy2, which will be described later, are settable. In other words, the image readout system is configured in such a manner that the six fluorescent image readout modes and two density measurement modes are settable.

Figure 10:
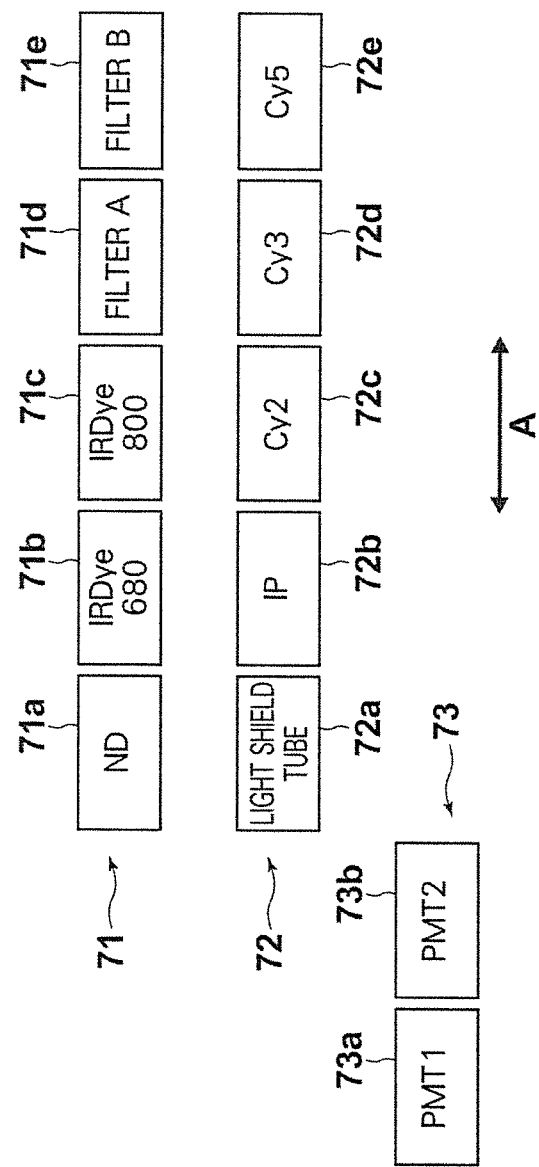
FIG. 10 is a diagram illustrating the initial positions of the first and second filter magazines and the light detection unit.

FIG. 10 illustrates an example of the kinds of the first through fifth filters 71a through 71e in the first filter magazine 71 and the kinds of the sixth through ninth filters 72b through 72e in the second filter magazine 72, and the relative positional relationship among the first and second filter magazines 71, 72 and the light detection unit 73 with respect to the direction of arrow A before a readout mode is set. Here, the direction of arrow A, illustrated in FIG. 10, corresponds to X direction in FIG. 3.

Further, in FIG. 10 through FIG. 18, an ND (Neutral Density) filter is represented by "ND", a filter for detecting fluorescence of IRDye680 is represented by "IRDye680", a filter for detecting fluorescence of IRDye800 is represented by "IRDye800", a filter for detecting fluorescence of a storable phosphor sheet (IP (imaging plate)) is represented by "IP", a filter for detecting fluorescence of Cy2 is represented by "Cy2", a filter for detecting fluorescence of Cy3 is represented by "Cy3", and a filter for detecting fluorescence of Cy5 is represented by "Cy5".

In the present embodiment, with respect to the first filter magazine 71 in the upper stage, an ND filter is placed as the first filter 71a, and a filter that selectively transmits fluorescence L emitted from IRDye680 and cuts excitation light E is placed as the second filter 71b. A filter that selectively transmits fluorescence L emitted from IRDye800 and cuts excitation light E is placed as the third filter 71c. Further, filter A and filter B, which are not used in the aforementioned modes but arbitrarily selected by a user, are placed as the fourth and fifth filters 71d, 71e.

With respect to the second filter magazine 72 in the lower stage, a filter that selectively transmits fluorescence L emitted from a storable phosphor sheet and cuts excitation light E is placed as the sixth filter 72b, and a filter that selectively transmits fluorescence L emitted from Cy2 and cuts excitation light E is placed as the seventh filter 72c. Further, a filter that selectively transmits fluorescence L emitted from Cy3 and cuts excitation light E is placed as the eighth filter 72d, and a filter that selectively transmits fluorescence L emitted from Cy5 and cuts excitation light E is placed as the ninth filter 72e.

Meanwhile, in the first and second density measurement modes, fluorescence L emitted from Cy3 and Cy2 is not detected, but fluorescence L emitted from a fluorescent plate is detected as described above. However, in the first density measurement mode, the sample 22 and the fluorescent plate are illuminated with excitation light E having a wavelength similar to the wavelength (532 nm) of excitation light E used to excite Cy3. Therefore, the filter for detecting fluorescence of Cy3 (the eighth filter 72b) is used. In the second density measurement mode, the sample 22 and the fluorescent plate are illuminated with excitation light E having a wavelength similar to the wavelength (488 nm) of excitation light E used to excite Cy2. Therefore, the filter for detecting fluorescence of Cy2 (the seventh filter 72c) is used.

The apparatus is structured in such a manner that light detection unit 73 is placed so as not to be under the first and second filter magazines 71 72 before a readout mode is set, and external light does not enter the first and second photomultipliers 73a, 73b in the light detection unit 70.

Figure 11:
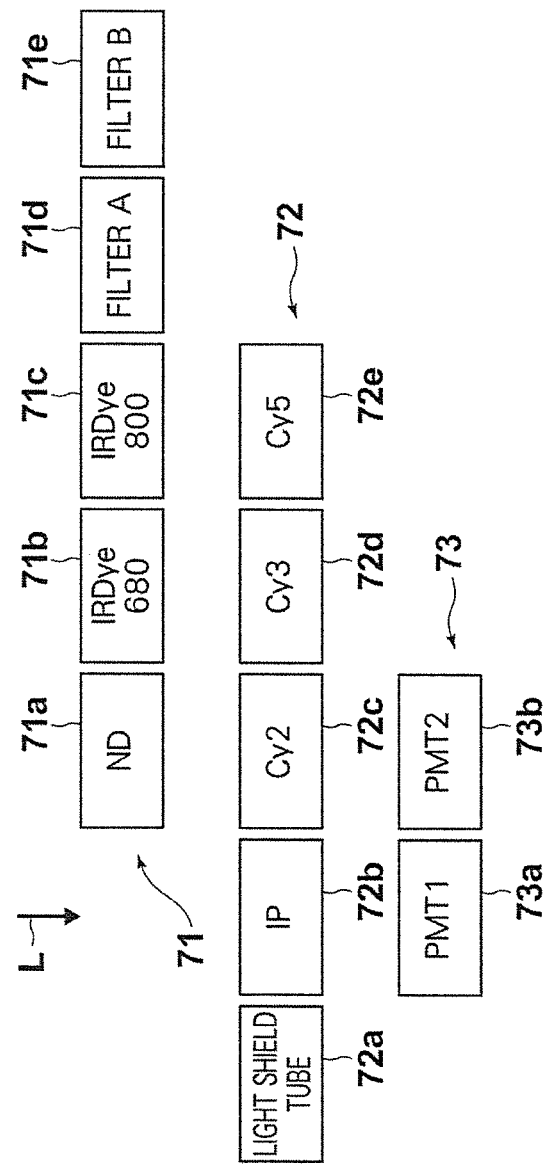
FIG. 11 is a diagram illustrating relative positional relationships among the first and second filter magazines and the light detection unit in a case where a first fluorescent image readout mode has been set.

FIG. 11 is a diagram illustrating relative positional relationships among the first and second filter magazines 71, 72 and the light detection unit 73 in a case where the first fluorescent image readout mode has been set. In a case where the first fluorescent image mode has been set, the drive of the first conveyance belt mechanism 82, the second conveyance belt mechanism 84 and the linear motor 85 is controlled by the control unit 11. Accordingly, the first and second filter magazines 71, 72 and the light detection unit 73 are placed, as illustrated in FIG. 11.

Specifically, in the first fluorescent image readout mode, the drive of the first and second conveyance belt mechanisms 82, 84 is controlled in such a manner that fluorescence L enters only the seventh filter 72b in the second filter magazine 72 in the lower stage, and the drive of the linear motor 85 is controlled in such a manner that fluorescence L is detected by the first photomultiplier 73a.

Figure 12:
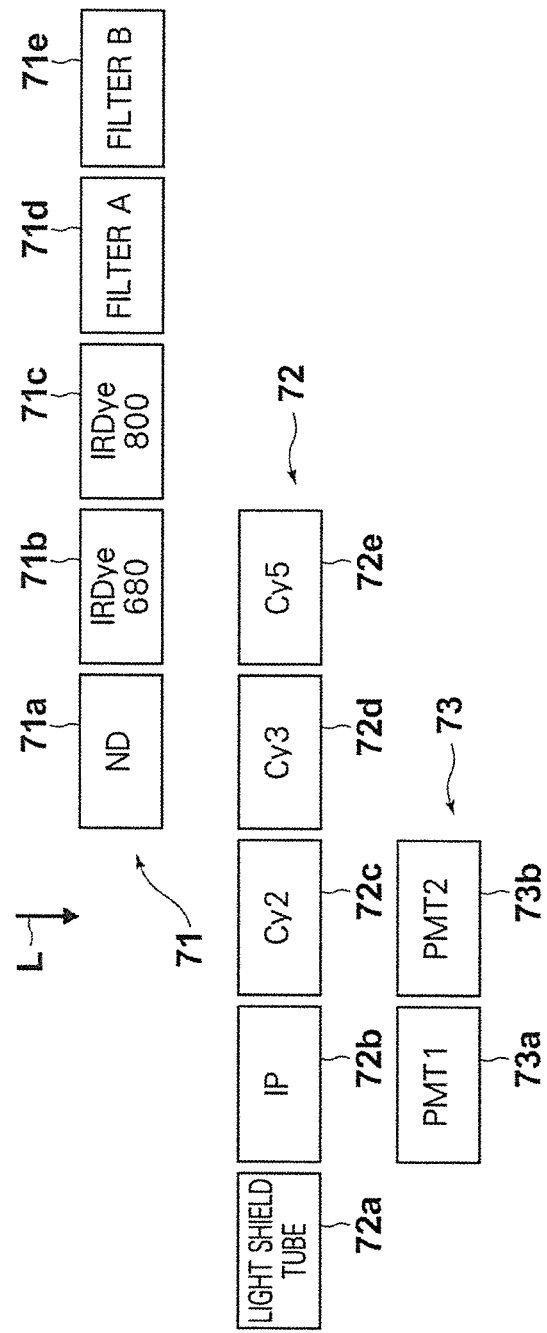
FIG. 12 is a diagram illustrating relative positional relationships among the first and second filter magazines and the light detection unit in a case where a second fluorescent image readout mode has been set.

FIG. 12 is a diagram illustrating relative positional relationships among the first and second filter magazines 71, 72 and the light detection unit 73 in a case where the second fluorescent image readout mode has been set.

In the second fluorescent image readout mode, the drive of the first and second conveyance belt mechanisms 82, 84 is controlled in such a manner that fluorescence L enters only the seventh filter 72c in the second filter magazine 72 in the lower stage, and the drive of the linear motor 85 is controlled in such a manner that fluorescence L is detected by the second photomultiplier 73b.

Figure 13:
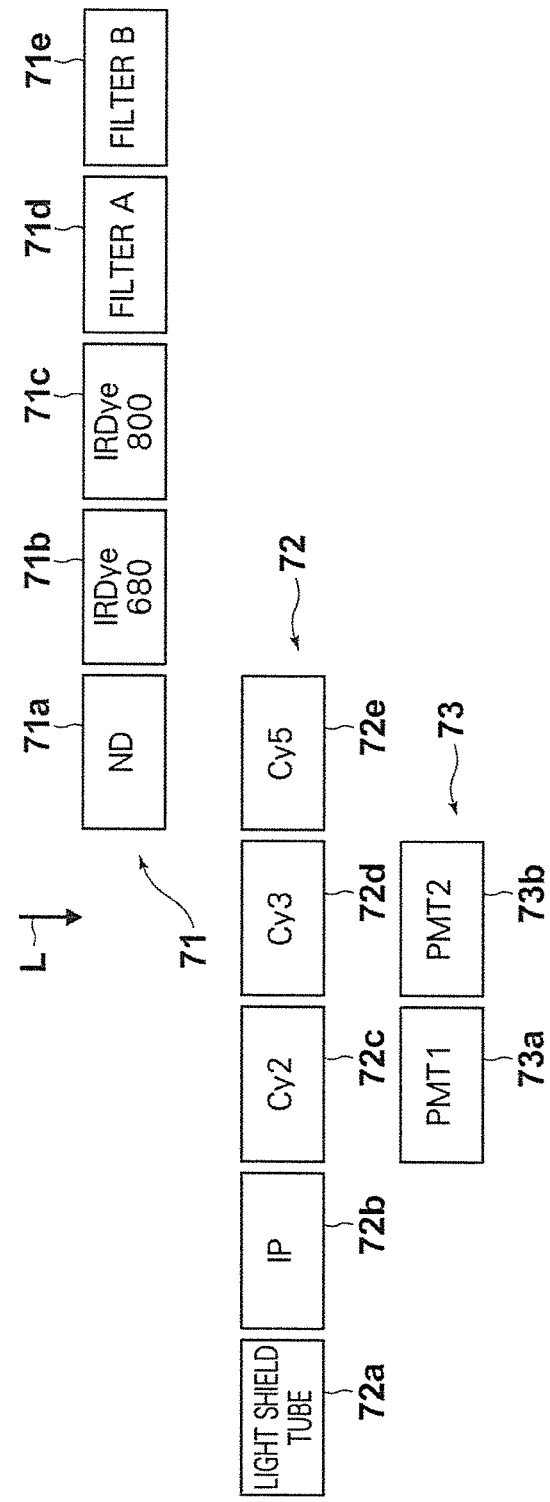
FIG. 13 is a diagram illustrating relative positional relationships among the first and second filter magazines and the light detection unit in a case where a third fluorescent image readout mode has been set.

FIG. 13 is a diagram illustrating relative positional relationships among the first and second filter magazines 71, 72 and the light detection unit 73 in a case where the third fluorescent image readout mode has been set.

In the third fluorescent image readout mode, the drive of the first and second conveyance belt mechanisms 82, 84 is controlled in such a manner that fluorescence L enters only the eighth filter 72d in the second filter magazine 72 in the lower stage, and the drive of the linear motor 85 is controlled in such a manner that fluorescence L is detected by the second photomultiplier 73b.

Figure 14:
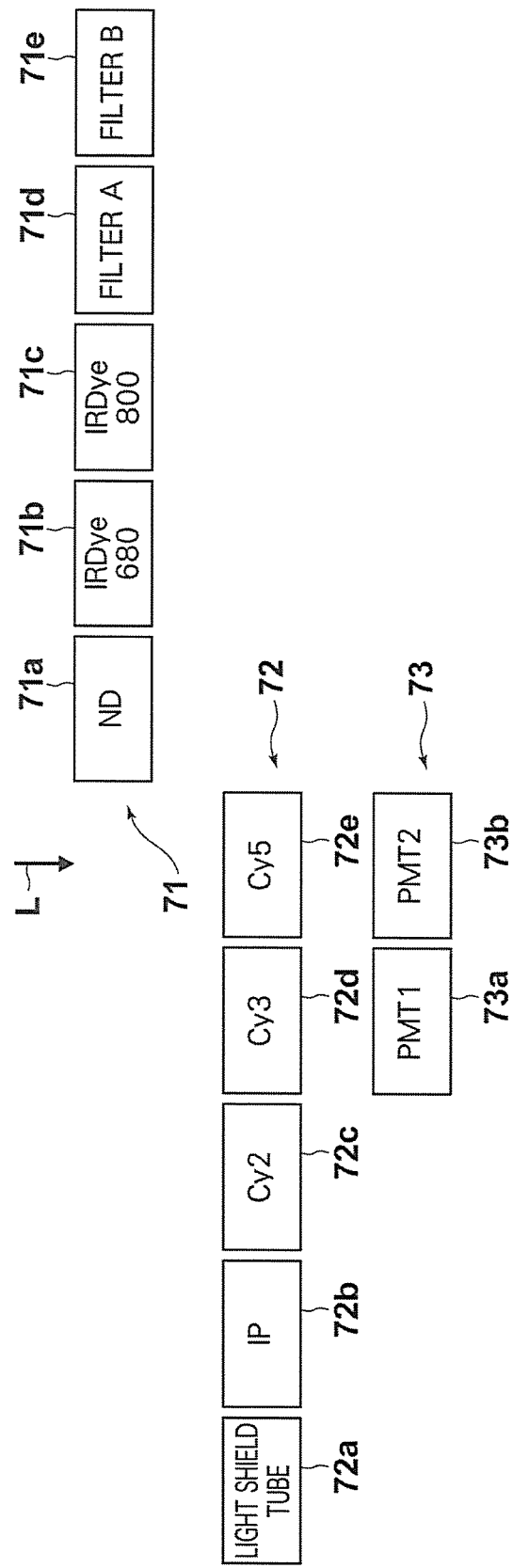
FIG. 14 is a diagram illustrating relative positional relationships among the first and second filter magazines and the light detection unit in a case where a fourth fluorescent image readout mode has been set.

FIG. 14 is a diagram illustrating relative positional relationships among the first and second filter magazines 71, 72 and the light detection unit 73 in a case where the fourth fluorescent image readout mode has been set.

In the fourth fluorescent image readout mode, the drive of the first and second conveyance belt mechanisms 82, 84 is controlled in such a manner that fluorescence L enters only the ninth filter 72e in the second filter magazine 72 in the lower stage, and the drive of the linear motor 85 is controlled in such a manner that fluorescence L is detected by the second photomultiplier 73b.

Figure 15:
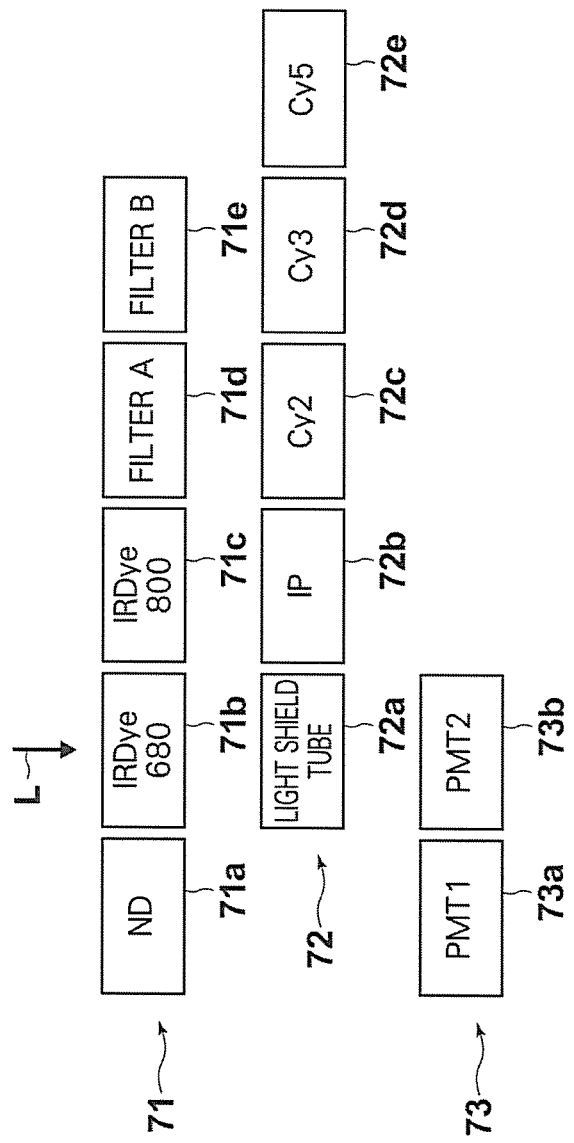
FIG. 15 is a diagram illustrating relative positional relationships among the first and second filter magazines and the light detection unit in a case where a fifth fluorescent image readout mode has been set.

FIG. 15 is a diagram illustrating relative positional relationships among the first and second filter magazines 71, 72 and the light detection unit 73 in a case where the fifth fluorescent image readout mode has been set.

In the fifth fluorescent image readout mode, the drive of the first and second conveyance belt mechanisms 82, 84 is controlled in such a manner that fluorescence L enters the second filter 71b in the first filter magazine 71 in the upper stage and the light shield tube 72a in the second filter magazine 72 in the lower stage, and the drive of the linear motor 85 is controlled in such a manner that fluorescence L is detected by the second photomultiplier 73b.

Figure 16:
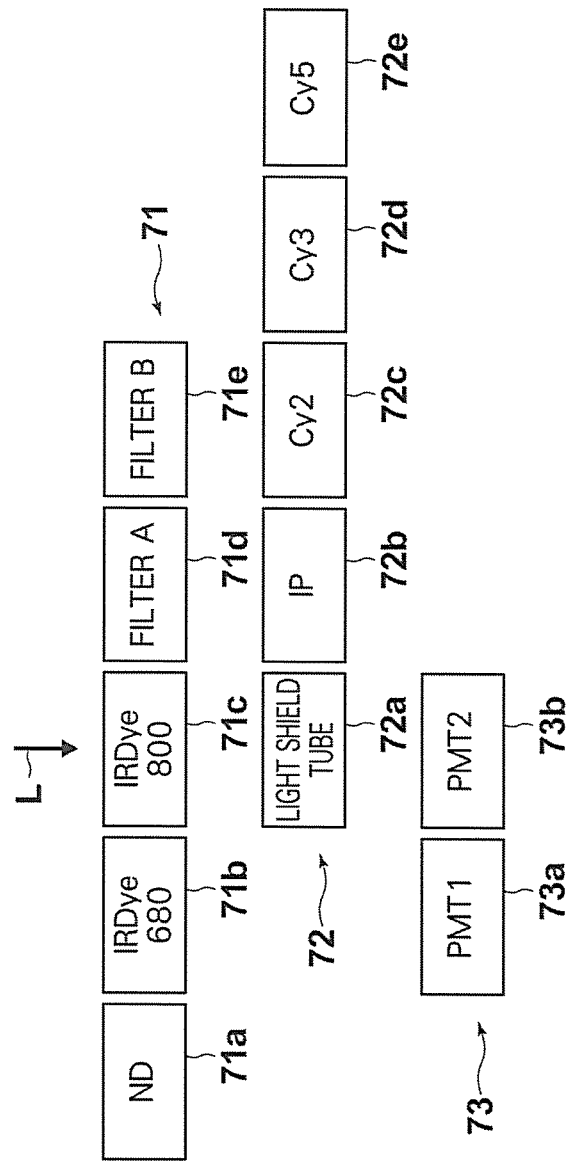
FIG. 16 is a diagram illustrating relative positional relationships among the first and second filter magazines and the light detection unit in a case where a sixth fluorescent image readout mode has been set.

FIG. 16 is a diagram illustrating relative positional relationships among the first and second filter magazines 71, 72 and the light detection unit 73 in a case where the sixth fluorescent image readout mode has been set.

In the sixth fluorescent image readout mode, the drive of the first and second conveyance belt mechanisms 82, 84 is controlled in such a manner that fluorescence L enters the third filter 71c in the first filter magazine 71 in the upper stage and the light shield tube 72a in the second filter magazine 72 in the lower stage, and the drive of the linear motor 85 is controlled in such a manner that fluorescence L is detected by the second photomultiplier 73b.

Figure 17:
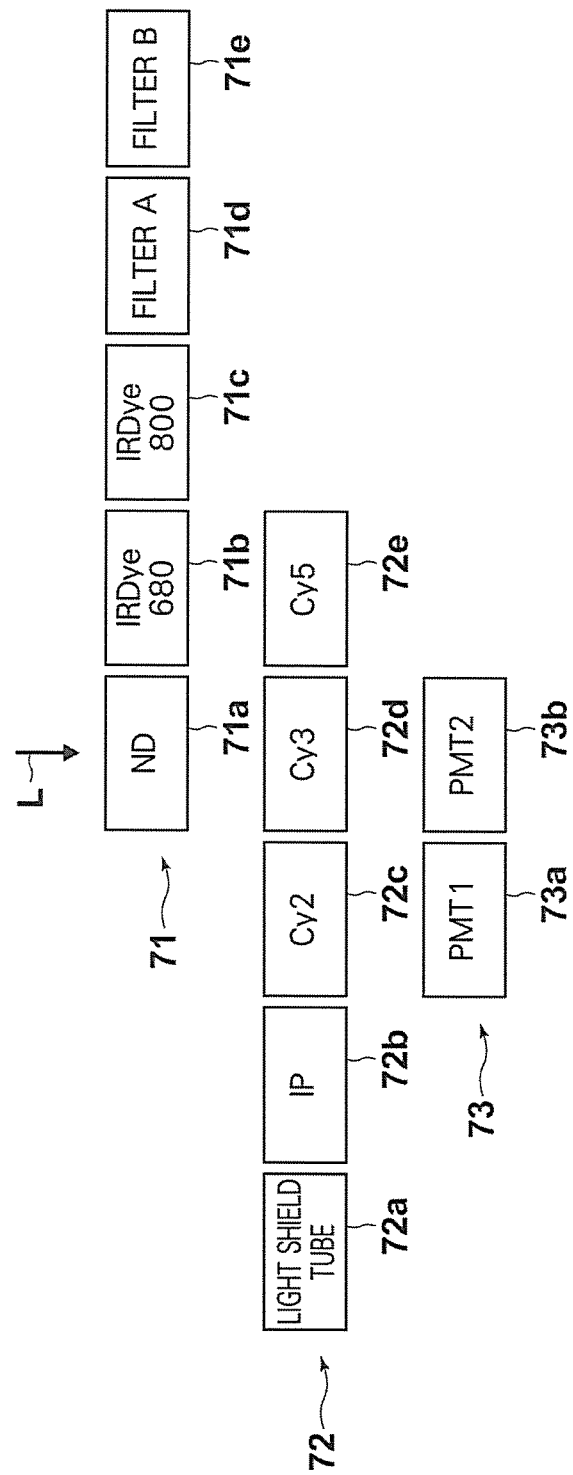
FIG. 17 is a diagram illustrating relative positional relationships among the first and second filter magazines and the light detection unit in a case where a first density measurement mode has been set.

FIG. 17 is a diagram illustrating relative positional relationships among the first and second filter magazines 71, 72 and the light detection unit 73 in a case where the first density measurement mode has been set. In the first density measurement mode, a fluorescent plate is set on the sample 22, as described above. This fluorescent plate may be set directly on the sample 22. Alternatively, the fluorescent plate may be set in such a manner that a space is formed between the fluorescent plate and the sample 22 by supporting the fluorescent plate using a support member or the like.

Further, the sample 22 is scanned with excitation light E of 532 nm by using the second excitation light source 52 in a similar manner to detection of fluorescence of Cy3. Excitation light E that has illuminated the sample 22 passes through the sample 22, and illuminates the fluorescent plate. Fluorescence L that has been emitted from the fluorescent plate by illumination with excitation light E enters the optical head 23 after passing through the sample 22. Further, fluorescence L is detected by the detection unit 70. It is possible to detect the optical density of the sample 22 by detecting fluorescence that has passed through the sample 22 in this manner. The sample 22 is, for example, a gel support body including protein dyed with CBB or dyed with silver, or the like.

Further, in the first density measurement mode, the drive of the first and second conveyance belt mechanisms 82, 84 is controlled in such a manner that fluorescence L enters the first filter 71a in the first filter magazine 71 in the upper stage and the eighth filter 72d in the second filter magazine 72 in the lower stage, and the drive of the linear motor 85 is controlled in such a manner that fluorescence L is detected by the second photomultiplier 73b.

Figure 18:
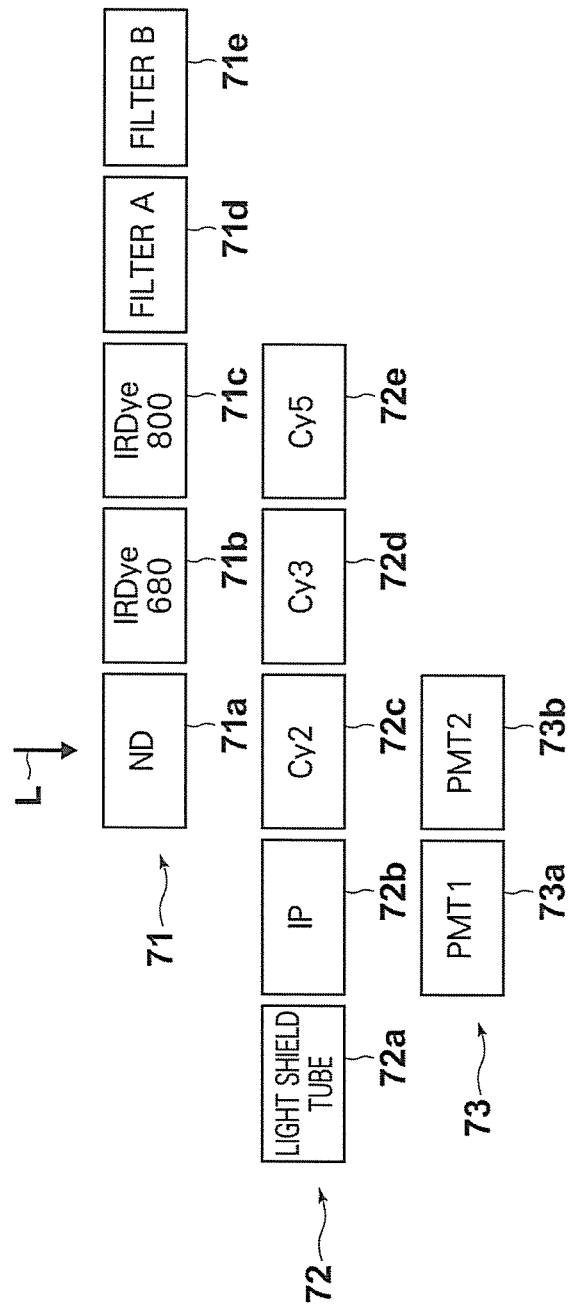
FIG. 18 is a diagram illustrating relative positional relationships among the first and second filter magazines and the light detection unit in a case where a second density measurement mode has been set.

FIG. 18 is a diagram illustrating relative positional relationships among the first and second filter magazines 71, 72 and the light detection unit 73 in a case where the second density measurement mode has been set. Here, a fluorescent plate is set on the sample 22 as described above also in the second density measurement mode.

Further, the sample 22 is scanned with excitation light E of 488 nm by using the first excitation light source 51 in a similar manner to detection of fluorescence of Cy2. Excitation light E that has illuminated the sample 22 passes through the sample 22, and illuminates the fluorescent plate. Fluorescence L that has been emitted from the fluorescent plate by illumination with excitation light E enters the optical head 23 after passing through the sample 22. Further, fluorescence L is detected by the detection unit 70.

Further, in the second density measurement mode, the drive of the first and second conveyance belt mechanisms 82, 84 is controlled in such a manner that fluorescence L enters the first filter 71a in the first filter magazine 71 in the upper stage and the seventh filter 72c in the second filter magazine 72 in the lower stage, and the drive of the linear motor 85 is controlled in such a manner that fluorescence L is detected by the second photomultiplier 73b.

As described above, the relative positional relationships among the first and second filter magazines 71, 72 and the light detection unit 73 are controlled based on each readout mode.

Next, back to FIG. 1, the image generation unit 12 generates a whole image signal of an image to be output to and displayed on the display apparatus 30 by performing signal processing on an input digital image signal. The whole image signal generated by the image generation unit 12 is displayed on the display apparatus 30 by the control unit 11.

The density measurement unit 13 calculates a density value by performing, on an input digital image signal, conversion processing that has been set in advance. A look-up table in which digital image signals and density values are correlated with each other or a function representing a relationship between them has been set in advance in the density measurement unit 13. The density measurement unit 13 calculates the density value by using the look-up table or the function.

The density value measured by the density measurement unit 13 is displayed, by text or graph, on the display apparatus 30 by the control unit 11.

Next, the action of the image readout system of the present embodiment will be described with reference to a flowchart illustrated in FIG. 19.

First, desirable first through fifth filters 71a through 71e are selected and set on the filter tray 100 in the first filter magazine 71. After then, the first filter magazine 71 is set on the first fixing rack 74 in the upper stage of the detection unit 70 (S10).

Further, the first and second filter magazines 71, 72 and the detection unit 73 are placed at initial setting positions, illustrated in FIG. 10 (S12). After then, information about metal piece patterns 79 provided for the first through fifth filters 71a through 71e in the first filter magazine 71 and information about metal piece patterns 79 provided for the light shield tube 72a and the sixth through ninth filters 72b through 72e in the second filter magazine 72 are read out by making the metal piece patterns 79 pass the first and second optical sensors 80, 86, respectively. The information is obtained by the control unit 11 (S14).

Next, a readout mode is set by an input by a user using the input apparatus 40 (S16). Information about the readout mode is obtained by the control unit 11. The control unit 11 controls the drive of the first and second conveyance belt mechanisms 82, 84 and the linear motor 85 based on the input readout mode. Accordingly, the first filter magazine 71, the second filter magazine 72 and the light detection unit 73 are moved, and placed at positions based on each readout mode as described above (S18).

Further, excitation light E is output from one of the first through fifth excitation light sources 51 through 55 based on the readout mode. The optical head 23 moves in X direction, and the optical head support substrate 41 moves in Y direction. Accordingly, the sample 22 is two-dimensionally scanned with excitation light E. Further, fluorescence L emitted from the sample 22 or the fluorescent plate set on the sample 22 sequentially enters the optical head 23. Fluorescence L that has entered the optical head 23 is reflected by the mirror 25 with a hole, and passes through at least one of the filters constituting the first and second filter magazines 71, 72, and detected by the first or second photomultiplier 73a, 73b (S20).

The analog image signal detected by the first or second photomultiplier 73a, 73b is stored in the storage unit 92 after being converted to a digital image signal by the A/D converter 91.

The digital image signal stored in the storage unit 92 is output to the image generation unit 12 in a case where one of the first through sixth fluorescent image readout modes has been set. The image generation unit 12 generates a whole image signal of an image by performing signal processing on the input digital image signal. The whole image signal is output to the control unit 11, and the control unit 11 displays, based on the input whole image signal, a fluorescent image of the sample 22 on the display apparatus (S22).

In a case where the first or second density measurement mode has been set, the digital image signal stored in the storage unit 92 is output to the density measurement unit 13, and the density measurement mode 13 calculates a density value based on the input digital image signal.

Further, the control unit 11 displays, by text or graph, the density value calculated by the density measurement unit 13 on the display apparatus 30 (S22).

According to the image readout system 1 of the above embodiment, the first and second filter magazines 71, 72 and the light detection unit 73 are placed in one direction in such a manner to be parallel to each other, and the first and second filter magazines 71, 72 and the light detection unit 73 are structured in such a manner to be movable in the arrangement direction of the filters. Therefore, fluorescence having different wavelengths from each other is detectable by the first or second photomultiplier 73a, 73b corresponding to the wavelengths of the fluorescence, respectively. Further, the size of the whole apparatus is reducible.

In the image readout system 1 of the above embodiment, the two filter magazines of the first and second filter magazines 71, 72 are used. Alternatively, three or more filter magazines may be placed one after another in one direction, and the system may be structured in such a manner that the three or more filter magazines are movable independently from each other.

What is claimed is:

1. A light detection apparatus comprising:
    a plurality of filter magazines in each of which a plurality of filters having different transmission wavelengths from each other are arranged in a row, and the plurality of filter magazines being arranged one after another in one direction; and
    a light detection unit in which a plurality of light detectors each of which detects light that has passed through at least one of the filters included in the plurality of filter magazines are arranged in the arrangement direction of the filters, and the light detection unit being placed in the one direction in such a manner to be parallel to the plurality of filter magazines,
    wherein the light detection apparatus is configured in such a manner that the plurality of filter magazines and the light detection unit are movable in the arrangement direction of the filters.

2. The light detection apparatus, as defined in claim 1, having a light shield tube for blocking external light at least at one position in one of the plurality of filter magazines that is placed toward the light detection unit.

3. The light detection apparatus, as defined in claim 1, further comprising:
    a control unit that obtains information about the kinds of the filters included in the filter magazines, and controls, based on the information about the kinds, the positions of the filter magazines in the arrangement direction of the filters.

4. The light detection apparatus, as defined in claim 3, further comprising:
    a filter information receiving unit that receives an input of the information about the kinds of the filters.

5. The light detection apparatus, as defined in claim 3, wherein the filters have filter information holding units that hold the information about the kinds of the filters.

6. The light detection apparatus, as defined in claim 1, wherein at least one of the plurality of filter magazines is detachable.

7. The light detection apparatus, as defined in claim 1, wherein at least one of the plurality of filters included in the filter magazines is detachable from the filter magazines.

8. The light detection apparatus, as defined in claim 1, wherein the plurality of filter magazines and the light detection unit are placed one after another in a vertical direction.

9. The light detection apparatus, as defined in claim 1, further comprising:
a linear motor that moves the light detection unit.

10. The light detection apparatus, as defined in claim 6, wherein the detachably structured filter magazine includes a filter tray on which the plurality of filters are placed one after another and lock levers that regulate the movement of the filter tray by being engaged with a light detection apparatus main body, and wherein the lock levers are rotatably provided at ends of the filter tray in the arrangement direction of the filters, and wherein fixing portions that fix rotation shafts of the lock levers to the filter tray are provided on inner surfaces of the ends of the filter tray.

11. The light detection apparatus, as defined in claim 10, wherein the filter magazine is mounted on the light detection apparatus main body by being inserted in a direction orthogonal to the arrangement direction of the filters, and wherein the lock levers are structured by members extending in the direction orthogonal to the arrangement direction of the filters, and also leading ends of the lock levers in an insertion direction to the light detection apparatus are bent inward with respect to the insertion direction.

* * * * *